(12) United States Patent
Hsin

(10) Patent No.: US 10,135,001 B1
(45) Date of Patent: Nov. 20, 2018

(54) ORGANIC ELECTROLUMINESCENT COMPOUND AND ORGANIC ELECTROLUMINESCENT DEVICE CONTAINING THE SAME

(71) Applicant: INT TECH CO., LTD., Hsinchu County (TW)

(72) Inventor: Meng-Hung Hsin, New Taipei (TW)

(73) Assignee: INT TECH CO., LTD., Hsinchu County (TW)

( * ) Notice: Subject to any disclaimer, the term of this patent is extended or adjusted under 35 U.S.C. 154(b) by 4 days.

(21) Appl. No.: 15/703,506

(22) Filed: Sep. 13, 2017

(51) Int. Cl.
| | |
|---|---|
| H01L 51/00 | (2006.01) |
| H01L 51/50 | (2006.01) |
| C09K 11/06 | (2006.01) |
| C07D 213/06 | (2006.01) |
| C07D 401/14 | (2006.01) |
| C07D 405/14 | (2006.01) |
| C07D 409/14 | (2006.01) |
| C07D 471/04 | (2006.01) |
| C07F 5/02 | (2006.01) |
| C07F 7/08 | (2006.01) |

(52) U.S. Cl.
CPC ........ *H01L 51/0067* (2013.01); *C07D 213/06* (2013.01); *C07D 401/14* (2013.01); *C07D 405/14* (2013.01); *C07D 409/14* (2013.01); *C07D 471/04* (2013.01); *C07F 5/027* (2013.01); *C07F 7/0812* (2013.01); *C09K 11/06* (2013.01); *H01L 51/0052* (2013.01); *H01L 51/0054* (2013.01); *H01L 51/0055* (2013.01); *H01L 51/0058* (2013.01); *H01L 51/0065* (2013.01); *H01L 51/0068* (2013.01); *H01L 51/0072* (2013.01); *H01L 51/0094* (2013.01); *C09K 2211/1011* (2013.01); *C09K 2211/1018* (2013.01); *H01L 51/5012* (2013.01); *H01L 51/5016* (2013.01)

(58) Field of Classification Search
CPC .................................................. C07C 2603/74
See application file for complete search history.

(56) References Cited

U.S. PATENT DOCUMENTS

2016/0147147 A1* 5/2016 Hirano .................. G03F 7/0045
430/18

* cited by examiner

*Primary Examiner* — Erich A Leeser
(74) *Attorney, Agent, or Firm* — WPAT, P.C., Intellectual Property Attorneys; Anthony King

(57) ABSTRACT

The present disclosure provides an organic electroluminescent compound represented by the formula (I):

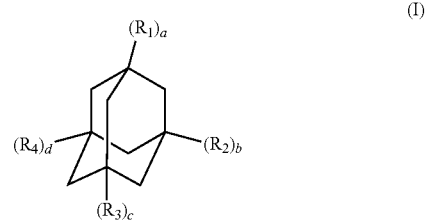

wherein $R_1$, $R_2$, $R_3$ and $R_4$ each independently represents a substituted or unsubstituted (C6-C30) aryl group, a substituted or unsubstituted 3- to 30-membered heteroaryl group, —NR5R6, —SiR7R8R9, —SR10, —OR11, a cyano group, a nitro group, or a hydroxyl group. The present disclosure further provides an organic electroluminescent device comprising the organic electroluminescent compound represented by the formula (I).

6 Claims, 1 Drawing Sheet

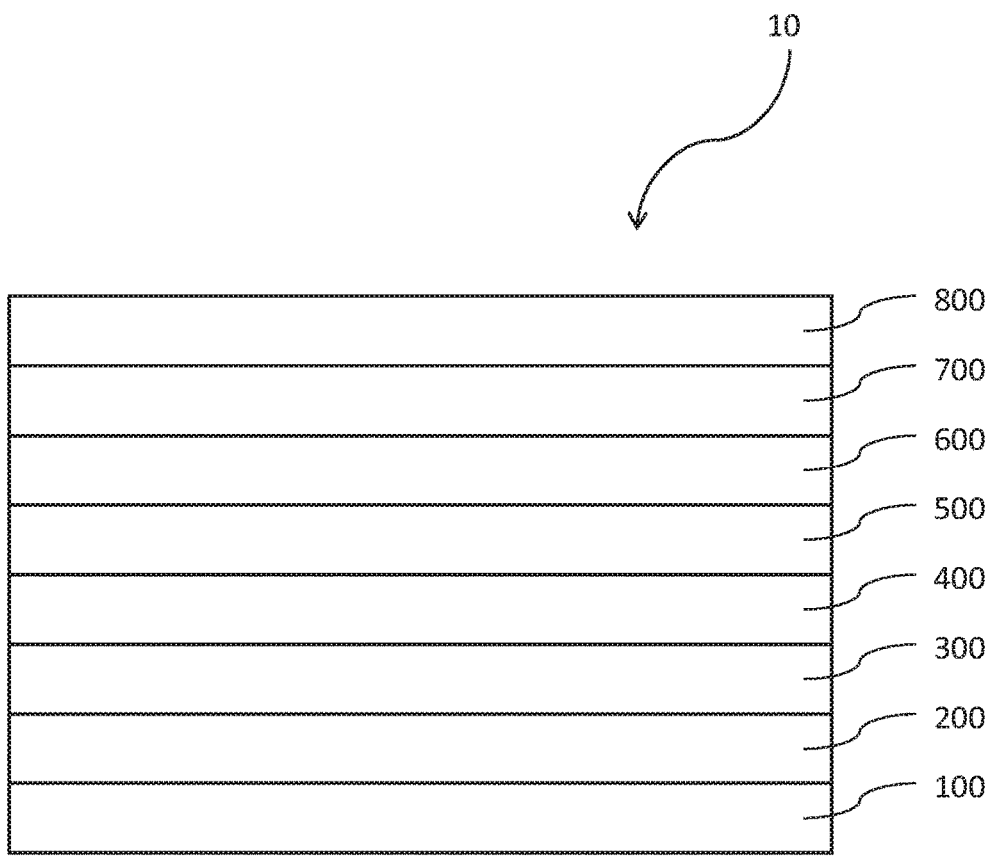

ORGANIC ELECTROLUMINESCENT COMPOUND AND ORGANIC ELECTROLUMINESCENT DEVICE CONTAINING THE SAME

BACKGROUND

Due to great potential application to flexible display devices, organic light emitting diodes (OLEDs) have recently become very important to the scientific community and the display industry, and now attract much focus in research and development. An OLED is a light-emitting diode (LED) in which a film of organic compounds is placed between two conductors and emits light in response to excitation such as by an electric current. OLEDs are useful in displays such as television screens, computer monitors, mobile phones, and tablets. OLED devices are self-luminous devices, and have been actively studied for their brightness, superior visibility, and the ability to display clearer images in comparison with liquid crystal devices.

However, the OLED device technology is currently experiencing an obstacle in the development process. A main issue is that light-emitting efficiency cannot meet practical demand, so the development of the OLED technology is greatly limited. One of the factors affecting the luminous efficiency of the OLED device is the efficiency of transporting carriers, including electrons and holes.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 1 is a view showing an embodiment of an organic electroluminescent device in accordance with some embodiments of the present disclosure.

DETAILED DESCRIPTION OF THE DISCLOSURE

The following disclosure provides many different embodiments, or examples, for implementing different features of the provided subject matter. Specific examples of components and arrangements are described below to simplify the present disclosure. These are, of course, merely examples and are not intended to be limiting.

OLED compounds rely on the radiative decay of molecular excited states (excitons) generated by recombination of electrons and holes in a host transport material. The nature of excitation results in interactions between electrons and holes that split the excited states into bright singlets and dark triplets. Traditional phosphorescent OLEDs rely on the mixing of singlet and triplet states due to spin-orbital (SO) interaction. This results in energy harvesting from all higher singlet and triplet states, followed by phosphorescence (relatively short-lived emission from the excited triplet). The shortened triplet lifetime reduces triplet exciton annihilation by charges and other excitons.

Therefore, there is a need for OLEDs that can reach higher excitation states without rapid degradation. It has now been discovered that thermally activated delayed fluorescence (TADF) can transfer population between singlet levels and triplet sublevels in a relevant timescale, such as, for example, 110 μs. The present disclosure provides organic electroluminescent compounds that are capable of fluorescing or phosphorescing at higher energy excitation states than the traditional organic electroluminescent compounds. The organic electroluminescent compounds of the present disclosure may improve carrier transporting ability. In some embodiments, the organic electroluminescent compounds of the present disclosure can be used in an electronic device or an optoelectronic device such as a light-emitting element, light-emitting device or lighting device.

In some embodiments, the present invention provides an organic electroluminescent compound represented by the following formula (I):

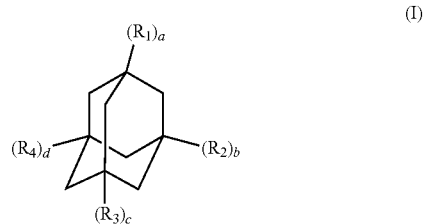

wherein $R_1$, $R_2$, $R_3$ and $R_4$ each independently represents a substituted or unsubstituted (C6-C30) aryl group, a substituted or unsubstituted 3- to 30-membered heteroaryl group, $-NR_5R_6$, $-SiR_7R_8R_9$, $-SR_{10}$, $-OR_{11}$, a cyano group, a nitro group or a hydroxyl group;

$R_5$ to $R_{11}$ each independently represents hydrogen, deuterium, a halogen, a substituted or unsubstituted (C1-C30) alkyl group, a substituted or unsubstituted (C6-C30) aryl group or a substituted or unsubstituted 3- to 30-membered heteroaryl group; or is linked to one or more adjacent substituents to form a mono- or polycyclic, alicyclic or aromatic ring whose carbon atom(s) may be replaced by at least one atom selected from nitrogen, oxygen and sulfur;

a and c each independently represents an integer of 1 to 3; wherein a or c is an integer of 1 or more, and each of $R_1$ or each of $R_3$ is the same or different;

b and d each independently represents an integer of 1 to 3; wherein b or d is an integer of 1 or more, and each of $R_2$ or each of $R_4$ is the same or different; and wherein the heteroaryl group contains at least one atom selected from B, N, O, S, P(=O), Si and P.

In some embodiments of the present disclosure, substituents of the substituted groups in $R_1$ to $R_4$ and $R_5$ to $R_{11}$ each independently includes at least one selected from the group consisting of deuterium, a halogen, a (C1-C30)alkyl group, a (C1-C30)alkyl group substituted with a halogen, a (C6-C30)aryl group, a 3- to 30-membered heteroaryl group, a 3- to 30-membered heteroaryl group substituted with a (C6-C30)aryl group, a (C6-C30)aryl group substituted with a 3- to 30-membered heteroaryl group, a (C3-C30)cycloalkyl group, a 5- to 7-membered heterocycloalkyl group, a tri(C1-C30)alkylsilyl group, a tri(C6-C30)arylsilyl group, a di(C1-C30)alkyl(C6-C30)arylsilyl group, a (C1-C30)alkyldi(C6-C30)arylsilyl group, a (C2-C30)alkenyl group, a (C2-C30)alkynyl group, a cyano group, a di(C1-C30)alkylamino group, a di(C6-C30)arylamino group, a (C1-C30)alkyl(C6-C30)arylamino group, a di(C6-C30)arylboronyl group, a di(C1-C30)alkylboronyl group, a (C1-C30)alkyl(C6-C30)arylboronyl group, a (C6-C30)aryl(C1-C30)alkyl group, a (C1-C30)alkyl(C6-C30)aryl group, a carboxyl group, a nitro group and a hydroxyl group.

In some embodiments of the present disclosure, the terms "alkyl" and "alkoxy," and any alkyl moiety that is comprised in substituents, include both a linear structure and a branched structure; and the term "cycloalkyl" includes a mono- or polycyclic hydrocarbon or a substituted or unsubstituted (C7-C30) bicycloalkyl group. The term "aryl" refers to an organic radical derived from an aromatic hydrocarbon by removing one hydrogen atom; includes a monocyclic ring or fused ring each of whose rings has 4 to 7, preferably 5 or 6, ring backbone atoms; may be formed by linking two or more aryl groups to one another via one or more single bonds; and includes phenyl, biphenyl, terphenyl, naphthyl, anthryl, indenyl, fluorenyl, phenanthrenyl, triphenylenyl, pyrenyl, perylenyl, chrysenyl, naphthacenyl, fluoranthenyl, etc., wherein said naphthyl includes 1-naphthyl and 2-naphthyl, said anthryl includes 1-anthryl, 2-anthryl and 9-anthryl, and said fluorenyl includes 1-fluorenyl, 2-fluorenyl, 3-fluorenyl, 4-fluorenyl and 9-fluorenyl. The term "heteroaryl" refers to an aryl having 1 to 4 heteroatoms selected from the group consisting of B, N, O, S, P(=O), Si and P, and carbon atoms as remaining ring backbone atoms other than said heteroatom; is a monocyclic ring or fused ring condensed with at least one benzene ring; may be partially saturated; may be formed by linking at least one heteroaryl group to another heteroaryl or aryl group via one or more single bonds; may be a divalent aryl group whose ring backbone heteroatom is oxidized or quaternarized, for example, to form an N-oxide or a quaternary salt; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., a fused ring-type heteroaryl including benzofuranyl, benzothiophenyl, isobenzofuranyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenanthridinyl, benzodioxolyl, dibenzofuranyl, dibenzothiophenyl, etc., N-oxides thereof (for example, pyridyl N-oxide, quinolyl N-oxide), and quaternary salts thereof.

In some embodiments of the present disclosure, $R_1$ to $R_4$ each independently represents hydrogen, deuterium, chloro, fluoro, methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl, decyl, dodecyl, hexadecyl, trifluoromethyl, perfluoroethyl, trifluoroethyl, perfluoropropyl, perfluorobutyl, phenyl, biphenyl, fluorenyl, fluoranthenyl, triphenylenyl, pyrenyl, chrysenyl, naphthacenyl, perylenyl, pyridyl, pyrrolyl, furanyl, thiophenyl, imidazolyl, benzoimidazolyl, indenyl, pyrazinyl, pyrimidinyl, pyridazinyl, quinolyl, triazinyl, benzofuranyl, dibenzofuranyl, benzothiophenyl, dibenzothiophenyl, pyrazolyl, indolyl, carbazolyl, thiazolyl, oxazolyl, benzothiazolyl, benzoxazolyl, phenanthrolinyl or N-carbazolyl.

In some embodiments of the present disclosure, each of $R_1$ to $R_4$ and $R_5$ to $R_{11}$ may independently be further substituted with at least one selected from the group consisting of deuterium, chloro, fluoro, methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl, decyl, dodecyl, hexadecyl, trifluoromethyl, perfluoroethyl, trifluoroethyl, perfluoropropyl, perfluorobutyl, phenyl, biphenyl, fluorenyl, fluoranthenyl, triphenylenyl, pyrenyl, chrysenyl, naphthacenyl, perylenyl, fluorotrimethylsilyl, triethylsilyl, tripropylsilyl, tri(t-butyl)silyl, t-butyldimethylsilyl, dimethylphenylsilyl, carbazolyl and triphenylsilyl, and more preferably at least one selected from the group consisting of deuterium, chloro, fluoro, methyl, ethyl, n-propyl, i-propyl, n-butyl, i-butyl, t-butyl, n-pentyl, i-pentyl, n-hexyl, n-heptyl, n-octyl, 2 ethylhexyl, n-nonyl and decyl.

Accordingly, in one embodiment, the present invention is an organic electroluminescent compound represented by the following formula (II):

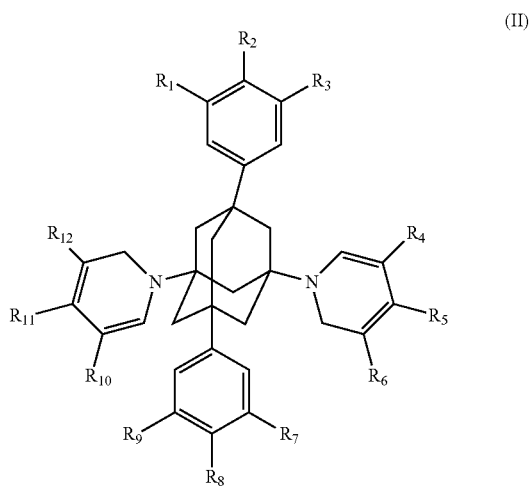

(II)

wherein $R_1$ to $R_{12}$ each independently represents hydrogen, deuterium, a halogen, a substituted or unsubstituted (C1-C30) alkyl group, a substituted or unsubstituted (C6-C30) aryl group or a substituted or unsubstituted 3- to 30-membered heteroaryl group; or is linked to one or more adjacent substituents to form a mono- or polycyclic, alicyclic or aromatic ring whose carbon atom(s) may be replaced by at least one atom selected from nitrogen, oxygen and sulfur; and the heteroaryl group contains at least one atom selected from B, N, O, S, P(=O), Si and P.

In some embodiments of the present disclosure, substituents of the substituted groups in $R_1$ to $R_{12}$ include independently at least one selected from the group consisting of deuterium, a halogen, a (C1-C30)alkyl group, a (C1-C30) alkyl group substituted with a halogen, a (C6-C30)aryl group, a 3- to 30-membered heteroaryl group, a 3- to 30-membered heteroaryl group substituted with a (C6-C30) aryl group, a (C6-C30)aryl group substituted with a 3- to 30-membered heteroaryl group, a (C3-C30)cycloalkyl group, a 5- to 7-membered heterocycloalkyl group, a tri(C1-C30)alkylsilyl group, a tri(C6-C30)arylsilyl group, a di(C1-C30)alkyl(C6-C30)arylsilyl group, a (C1-C30)alkyldi(C6-C30)arylsilyl group, a (C2-C30)alkenyl group, a (C2-C30) alkynyl group, a cyano group, a di(C1-C30)alkylamino group, a di(C6-C30)arylamino group, a (C1-C30)alkyl(C6-C30)arylamino group, a di(C6-C30)arylboronyl group, a di(C1-C30)alkylboronyl group, a (C1-C30)alkyl(C6-C30) arylboronyl group, a (C6-C30)aryl(C1-C30)alkyl group, a (C1-C30)alkyl(C6-C30)aryl group, a carboxyl group, a nitro group, and a hydroxyl group.

In some embodiments of the present disclosure, the terms "alkyl" and "alkoxy," and any alkyl moiety which is comprised in substituents, include both a linear structure and a branched structure; and the term "cycloalkyl" includes a mono- or polycyclic hydrocarbon such as a substituted or unsubstituted (C7-C30) bicycloalkyl group. The term "aryl" refers to an organic radical derived from an aromatic hydrocarbon by removing one hydrogen atom; includes a monocyclic ring or fused ring each of whose rings has 4 to 7, preferably 5 or 6, ring backbone atoms; may be formed by linking two or more aryl groups to one another via one or more single bonds; and includes phenyl, biphenyl, terphenyl, naphthyl, anthryl, indenyl, fluorenyl, phenanthrenyl, triphenylenyl, pyrenyl, perylenyl, chrysenyl, naphthacenyl, fluoranthenyl, etc., wherein said naphthyl includes 1-naphthyl and 2-naphthyl, said anthryl includes 1-anthryl, 2-anthryl and 9-anthryl and said fluorenyl includes 1-fluorenyl, 2-fluorenyl, 3-fluorenyl, 4-fluorenyl and 9-fluorenyl. The term "heteroaryl" refers to an aryl having 1 to 4 heteroatoms selected from the group consisting of B, N, O, S, P($=$O), Si and P, and carbon atoms as remaining ring backbone atoms other than said heteroatom; is a monocyclic ring or fused ring condensed with at least one benzene ring; may be partially saturated; may be one formed by linking at least one heteroaryl group to other heteroaryl or aryl group via one or more single bonds; may be a divalent aryl group whose ring backbone heteroatom is oxidized or quaternarized, for example, to form an N-oxide or a quaternary salt; and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., a fused ring-type heteroaryl including benzofuranyl, benzothiophenyl, isobenzofuranyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenanthridinyl, benzodioxolyl, dibenzofuranyl, dibenzothiophenyl, etc., N-oxides thereof (for example, pyridyl N-oxide, quinolyl N-oxide), and quaternary salts thereof.

In some embodiments of the present disclosure, each of $R_1$ to $R_{12}$ may independently be further substituted with at least one selected from the group consisting of deuterium, chloro, fluoro, methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl, decyl, dodecyl, hexadecyl, trifluoromethyl, perfluoroethyl, trifluoroethyl, perfluoropropyl, perfluorobutyl, phenyl, biphenyl, fluorenyl, fluoranthenyl, triphenylenyl, pyrenyl, chrysenyl, naphthacenyl, perylenyl, fluorotrimethylsilyl, triethylsilyl, tripropylsilyl, tri(t-butyl)silyl, t-butyldimethylsilyl, dimethylphenylsilyl, carbazolyl and triphenylsilyl, and more preferably at least one selected from the group consisting of deuterium, chloro, fluoro, methyl, ethyl, n-propyl, i-propyl, n-butyl, i-butyl, t-butyl, n-pentyl, i-pentyl, n-hexyl, n-heptyl, n-octyl, 2 ethylhexyl, n-nonyl and decyl.

In some embodiments of the present disclosure, an organic electroluminescent device comprises: an anode, a cathode, and at least an emitting layer and an electron-transporting layer provided between the anode and the cathode; the emitting layer containing a host material which is the organic electroluminescent compound represented by the following formula (I):

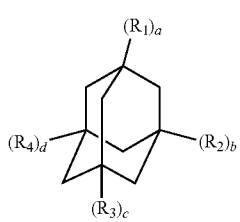

(I)

wherein
$R_1$, $R_2$, $R_3$ and $R_4$ each independently represents a substituted or unsubstituted (C6-C30) aryl group, a substituted or unsubstituted 3- to 30-membered heteroaryl group, $-NR_5R_6$, $-SiR_7R_8R_9$, $-SR_{10}$, $-OR_{11}$, a cyano group, a nitro group, or a hydroxyl group;

$R_5$ to $R_{11}$ each independently represents hydrogen, deuterium, a halogen, a substituted or unsubstituted (C1-C30) alkyl group, a substituted or unsubstituted (C6-C30) aryl group, or a substituted or unsubstituted 3- to 30-membered heteroaryl group; or is linked to one or more adjacent substituents to form a mono- or polycyclic, alicyclic or aromatic ring whose carbon atom(s) may be replaced by at least one atom selected from nitrogen, oxygen and sulfur;

a and c each independently represents an integer of 1 to 3; wherein a or c is an integer of 1 or more, and each of $R_1$ or each of $R_3$ is the same or different;

b and d each independently represents an integer of 1 to 3; wherein b or d is an integer of 1 or more, each of $R_2$ or each of $R_4$ is the same or different; and wherein the heteroaryl group contains at least one atom selected from B, N, O, S, P($=$O), Si and P.

In some embodiments of the present disclosure, an organic electroluminescent device comprises: an anode, a cathode, and at least an emitting layer and an electron-transporting layer provided between the anode and the cathode; the emitting layer containing a host material which is the organic electroluminescent compound represented by the following formula (II):

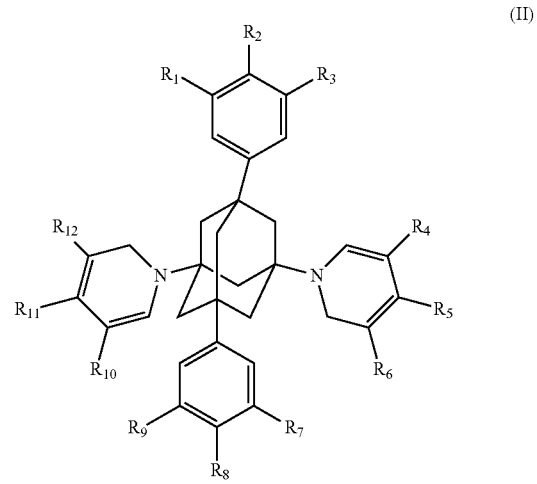

(II)

wherein $R_1$ to $R_{12}$ each independently represents hydrogen, deuterium, a halogen, a substituted or unsubstituted (C1-C30) alkyl group, a substituted or unsubstituted (C6-C30) aryl group, or a substituted or unsubstituted 3- to 30-membered heteroaryl group; or is linked to one or more adjacent substituents to form a mono- or polycyclic, alicyclic or aromatic ring whose carbon atom(s) may be replaced by at least one atom selected from nitrogen, oxygen and sulfur.

In some embodiments of the present disclosure, in an organic electroluminescent (EL) device comprising at least the emitting layer and an electron-transporting layer provided between a cathode and an anode, an emitting layer contains a host material which includes the organic electroluminescent compounds represented by the above-depicted formula (I) or (II).

FIG. 1 illustrates an example of the organic EL device according to some embodiments of the present invention. An organic EL device 10 has a configuration in which an anode 200, a hole-injecting layer 300, a hole-transporting layer 400, an emitting layer 500, an electron-transporting layer 600, an electron-injecting layer 700, and a cathode 800 are stacked on a substrate 100 in an order. In some embodiments, the emitting layer 500 contains a host material of the organic electroluminescent compound represented by the above-depicted formula (I). In some embodiments, the emitting layer 500 contains a host material of the organic electroluminescent compound represented by the above-depicted formula (II).

In some embodiments of the present disclosure, the organic EL device is an under surface emission type or bottom emission type where light is out through a substrate. In some embodiments, the organic EL device of the present disclosure is formed on a transparent substrate. In some embodiments, the transparent substrate is a substrate for supporting the organic EL device, and is preferably a flat and smooth substrate having a light ray transmittance of 50% or more. In some embodiments, the organic EL device is an upper surface emission type or top emission type where light is out from the upper part of the device, and a light-reflecting metal such as aluminum is provided on the above substrate.

In some embodiments of the present disclosure, in the organic electroluminescent device, a mixed region of an electron transport compound and a reductive dopant, or a mixed region of a hole transport compound and an oxidative dopant, may be placed on at least one surface of a pair of electrodes. In some embodiments, the electron transport compound is reduced to an anion, thus facilitating injection and transport of electrons from the mixed region to the electroluminescent medium. In some embodiments, the hole transport compound is oxidized to a cation, thus facilitating injection and transport of holes from the mixed region to the electroluminescent medium. In some embodiments, the oxidative dopant includes various Lewis acids and acceptor compounds, wherein the reductive dopant includes alkali metals, alkali metal compounds, alkaline earth metals, rare-earth metals, or mixtures thereof. In some embodiments, a reductive dopant layer may be employed as a charge-generating layer to prepare an electroluminescent device having two or more electroluminescent layers and emitting a white light.

In some embodiments of the present disclosure, the organic EL device comprises a first electrode, a second electrode and at least one organic layer between the first electrode and the second electrode. In some embodiments, the organic layer comprises a light-emitting layer. In some embodiments, the light-emitting layer comprises a composition for the organic electroluminescent device of the present disclosure and a phosphorous dopant. In some embodiments, the composition for the organic electroluminescent device comprises a host material.

In some embodiments of the present disclosure, the organic EL device may further comprise at least one compound selected from the group consisting of arylamine-based compounds and styrylarylamine-based compounds in the organic layer.

In some embodiments of the present disclosure, in the organic EL device, the organic layer may further comprise the organic electroluminescent compounds represented by the formulas (I) and (II), at least one metal selected from the group consisting of metals of Group 1, metals of Group 2, transition metals of the 4th period, transition metals of the 5th period, lanthanides and organic metals of d-transition elements of the Periodic Table, or at least one complex compound comprising the metals. In some embodiments, the organic layer may further comprise a light-emitting layer and a charge-generating layer.

In some embodiments of the present disclosure, the organic EL device may emit a white light by further comprising at least one light-emitting layer which comprises a blue electroluminescent compound, a red electroluminescent compound or a green electroluminescent compound, in addition to the compound of the present disclosure. In some embodiments, the organic EL device may further comprise a yellow light-emitting layer or an orange light-emitting layer.

In some embodiments of the present disclosure, in the organic EL device, at least one layer (referred to as "a surface layer") selected from a chalcogenide layer, a metal-halide layer and a metal-oxide layer may be placed on one or more inner surfaces of one or both electrodes. In some embodiments, it is preferred that the chalcogenide (including oxides) layer of silicon or aluminum is placed on an anode surface of an electroluminescent medium layer, and the metal-halide layer or metal-oxide layer is placed on a cathode surface of an electroluminescent medium layer. Such a surface layer provides operational stability for the organic electroluminescent device. Preferably, said chalcogenide includes $SiO_X$ (1<X<2), $AlO_X$ (1<X<1.5), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

In some embodiments of the present disclosure, the use of an organic electroluminescent compound represented by the formula (I) or (II) as a host material in an organic EL device can provide an organic EL device with a practical efficiency and lifetime.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An organic electroluminescent compound represented by the following formula (I):

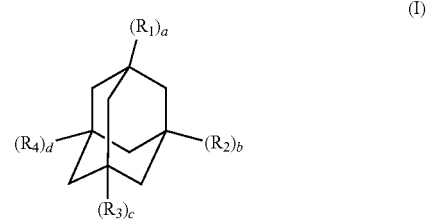

(I)

wherein $R_1$, $R_2$, $R_3$ and $R_4$ each independently represents a substituted or unsubstituted (C6-C30) aryl group, a substituted or unsubstituted 3- to 30-membered heteroaryl group, —NR$_5$R$_6$, —SiR$_7$R$_8$R$_9$, —SR$_{10}$, —OR$_{11}$, a cyano group, a nitro group or a hydroxyl group;

R$_5$ to R$_{10}$ each independently represents hydrogen, deuterium, a halogen, a substituted or unsubstituted (C1-C30) alkyl group, a substituted or unsubstituted (C6-C30) aryl group or a substituted or unsubstituted 3- to 30-membered heteroaryl group; or is linked to one or more adjacent substituents to form a mono- or polycyclic, alicyclic or aromatic ring whose carbon atom(s) may be replaced by at least one atom selected from nitrogen, oxygen and sulfur;

R$_{11}$ represents hydrogen, deuterium or a halogen; or is linked to one or more adjacent substituents to form a mono- or polycyclic, alicyclic or aromatic ring whose carbon atom(s) may be replaced by at least one atom selected from nitrogen, oxygen and sulfur;

a and c each independently represents an integer of 1 to 3; wherein a or c is an integer of 1 or more, and each of R$_1$ or each of R$_3$ is the same or different;

b and d each independently represents an integer of 1 to 3; wherein b or d is an integer of 1 or more, and each of R$_2$ or each of R$_4$ is the same or different; and wherein the heteroaryl group contains at least one atom selected from B, N, O, S, P(=O), Si and P.

2. The organic electroluminescent compound of claim 1, wherein each of the substituents of the substituted groups in R$_1$ to R$_4$ and R$_5$ to R$_{10}$ independently includes at least one selected from the group consisting of deuterium, a halogen, a (C1-C30)alkyl group, a (C1-C30)alkyl group substituted with a halogen, a (C6-C30)aryl group, a 3- to 30-membered heteroaryl group, a 3- to 30-membered heteroaryl group substituted with a (C6-C30)aryl group, a (C6-C30)aryl group substituted with a 3- to 30-membered heteroaryl group, a (C3-C30)cycloalkyl group, a 5- to 7-membered heterocycloalkyl group, a tri(C1-C30)alkylsilyl group, a tri(C6-C30)arylsilyl group, a di(C1-C30)alkyl(C6-C30)arylsilyl group, a (C1-C30)alkyldi(C6-C30)arylsilyl group, a (C2-C30)alkenyl group, a (C2-C30)alkynyl group, a cyano group, a di(C1-C30)alkylamino group, a di(C6-C30)arylamino group, a (C1-C30)alkyl(C6-C30)arylamino group, a di(C6-C30)arylboronyl group, a di(C1-C30)alkylboronyl group, a (C1-C30)alkyl(C6-C30)arylboronyl group, a (C6-C30)aryl(C1-C30)alkyl group, a (C1-C30)alkyl(C6-C30)aryl group, a carboxyl group, a nitro group, and a hydroxyl group.

3. The organic electroluminescent compound of claim 2, wherein each of R$_1$ to R$_4$ independently represents phenyl, biphenyl, fluorenyl, fluoranthenyl, triphenylenyl, pyrenyl, chrysenyl, naphthacenyl, perylenyl, pyridyl, pyrrolyl, furanyl, thiophenyl, imidazolyl, benzoimidazolyl, indenyl, pyrazinyl, pyrimidinyl, pyridazinyl, quinolyl, triazinyl, benzofuranyl, dibenzofuranyl, benzothiophenyl, dibenzothiophenyl, pyrazolyl, indolyl, carbazolyl, thiazolyl, oxazolyl, benzothiazolyl, benzoxazolyl, phenanthrolinyl or N-carbazolyl.

4. The organic electroluminescent compound of claim 1, wherein each of R$_1$ to R$_4$ or R$_5$ to R$_{10}$ is independently substituted with at least one selected from the group consisting of deuterium, chloro, fluoro, methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl, decyl, dodecyl, hexadecyl, trifluoromethyl, perfluoroethyl, trifluoroethyl, perfluoropropyl, perfluorobutyl, phenyl, biphenyl, fluorenyl, fluoranthenyl, triphenylenyl, pyrenyl, chrysenyl, naphthacenyl, perylenyl, fluorotrimethylsilyl, triethylsilyl, tripropylsilyl, tri(t-butyl)silyl, t-butyldimethylsilyl, dimethylphenylsilyl, carbazolyl and triphenylsilyl.

5. An organic electroluminescent device comprising:
an anode;
a cathode; and
an emitting layer provided between the anode and the cathode;
wherein the emitting layer containing a host material which is the organic electroluminescent compound of claim 1.

6. The organic electroluminescent compound of claim 1, wherein each of R$_1$ to R$_4$ or R$_5$ to R$_{10}$ is independently substituted with at least one selected from the group consisting of deuterium, chloro, fluoro, methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl and decyl.

* * * * *